United States Patent [19]

Christensen

[11] Plant 4,356

[45] Dec. 26, 1978

[54] MINIATURE MOSS ROSE PLANT

[75] Inventor: Jack E. Christensen, San Dimas, Calif.

[73] Assignee: Armstrong Nurseries, Inc., Ontario, Calif.

[21] Appl. No.: 864,245

[22] Filed: Dec. 27, 1977

[51] Int. Cl.[2] ..... A01H 5/00

[52] U.S. Cl. ..... Plt./10

[58] Field of Search ..... Plt./10

*Primary Examiner*—Robert E. Bagwill

*Attorney, Agent, or Firm*—Andrew R. Klein

[57] ABSTRACT

A dwarf bush rose of the hybrid miniature moss rose class. The plant has many moss-scented stipitate glands on its penduncles, buds, sepals and hips, and blooms almost continuously throughout the growing season. The overall color effect of the flowers is a deep velvety red. There are from about 40 to about 50 relatively broad petals in the flower, with from 7 to 20 petaloids. The plant manifests a better-than-average resistance to mildew, as compared to roses of its class under parallel conditions.

1 Drawing Figure

This invention relates to a hybrid miniature moss rose of the dwarf type. The plant is a bush outdoor seedling, cultivated primarily for cut flowers and garden decoration. Its hardiness has not yet been tested. For purposes of varietal identification, it has been given the denomination: "ARON". Its seed parent was "Fairy Moss" (U.S. Plant Pat. No. 3,083), and the pollen parent was "Rubinette" (U.S. Plant Pat. No. 3,383). The plant was first produced in Ontario, Calif., and the descriptive references to the plant and its bloom hereinafter will relate to plants of the same class grown in this region. The plant preserves its distinguishing characteristics through succeeding propagations by cuttings and by budding.

The new variety may be most readily distinguished from its seed parent, Fairy Moss, first, by the velvety red coloration of the flowers, while Fairy Moss has deep pink blooms. Second, the flowers of the new rose comprise about 40 to 50 petals, plus numerous petaloids, whereas Fairy Moss is semi-double, with less than half as many petals. Furthermore, flowers of the new cultivar open relatively slowly, while retaining a high-pointed center, whereas the flowers of Fairy Moss open rather quickly and are flat.

Among the characteristics which distinguish the new variety from its pollen parent, Rubinette, the following may be especially noted:

The new rose is a hybrid miniature moss rose with many moss-scented stipitate glands on its peduncles, buds, sepals and hips, but its pollen parent, Rubinette, is a floribunda rose without "mossy" characteristics.

The mature height of the new cultivar is generally less than half of the outdoor plant height of its pollen parent, Rubinette. Furthermore, the new cultivar is grown primarily as an outdoor garden rose, while Rubinette is grown mainly as a greenhouse forcing rose.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

Unless otherwise indicated, comparative terms herein are intended to relate the new variety to other roses of the miniature class. Thus, "average" as applied to size, means "average" as compared to miniatures generally, rather than to hybrid Tea roses, for example. The descriptive matter which follows pertains to roses grown in the environment of Southern California, and is believed to be applicable to similar conditions of soil and climate elsewhere.

FLOWER

The flowers are sometimes borne singly, but usually 2 to 4 on a stem, in irregular clusters. The stems are strong and of medium to long length, for miniatures. The quantity of bloom is abundant, outdoors, and persists almost continuously throughout the growing season. The blooms have a slight tea to damask fragrance.

Bud

The peduncle is of average length, of relatively heavy caliper, erect and stiff. It bears numerous stipitate glands and numerous prickles. It is between Strong Yellow Green, 5GY6/8, and Moderate Yellow Green, 5GY5/6, in color.

Before the calyx breaks, the bud is medium in size for miniatures, of medium length, pointed and ovoid. On the surface of the bud is light moss in the form of numerous scented stipitate glands, and slender foliaceous parts usually extend beyond the tip of the bud equal to one-quarter or more of its length.

As the calyx breaks, the color is near Dark Red, 2.5R3/7. The inner surface of the sepals carries a fine tomentum, while margins of the sepals are lined with stipitate glands and/or fine hairs.

As the first petal opens, the bud is average to large in size for miniatures, medium-length and pointed and ovoid to urn-shaped. The color on the outside of the petal is between Moderate Red, 2.5R4/10, and Dark Red, 2.5R3/7, with a small area near the base near Brilliant Yellow Green, 2.5GY9/8. The inside surface of the petal is a richer color than a color between Strong Red, 5R4/12, and Dark Red, 2.5R3/7. The bud opens up well and is not retarded from opening by cold, hot, wet or dry weather.

Bloom

The size of the bloom when fully open is average to large for miniatures, ranging from 3½ to 5 centimeters in diameter. The petalage is double, with from about 40 to about 50 petals, plus about 7 to 20 petaloids arranged regularly. The bloom is high centered at first, opening slowly with a distinctly pointed center, and becoming open to high centered. The petals remain at first somewhat tightly cupped with tips and/or margins reflexed outward, becoming later at maturity more loosely cupped, with tips and/or margins reflexed outward.

Petals

The petals are relatively thick and moderately leathery, with inside velvety and outside slightly shiny to satiny. The outside petals are nearly round to very broadly obovate. Intermediate petals are broadly obovate, while inside petals are obovate to broadly obovate. The colors may be modified by being striped, blotched, shaded and/or washed with other colors.

The paragraph immediately following describes color values observed in a flower newly opened in the month of August. The plant had been grown outdoors, in Ontario, Calif.

The outer surfaces of all petals, both outside, intermediate and inside, were of the same coloration, being between Moderate Red, 2.5R4/10, and Deep Purplish Red, 10RP3/10, with a small area at the base between white and Brilliant Yellow Green, 2.5GY9/8. The inner surfaces of all petals were likewise of the same coloration, being more brilliant than a color between Strong Red, 5R4/12, and Dark Red, 5R3/7, with a small area near the base between white and Brilliant Yellow Green, 2.5GY9/8.

The paragraphs immediately following describe the color values observed in a bloom which had been fully open for three days, outdoors, in the month of August. The plant was grown outdoors in Ontario, Calif.

The outer surface of the outside petal was between Moderate Red, 2.5R4/10, and Dark Red, 2.5R3/7, with a very small area near the base between white and Brilliant Yellow Green, 2.5GY9/8. The inner surface of the outside petal was less brilliant than on the newly opened flower but more brilliant than a color between Strong Red, 5R4/12, and Deep Red, 2.5R3/7, with a small area at the base between white and Brilliant Yellow Green, 2.5GY9/8.

The outer surface of the inside petal was between Strong Purplish Red, 10RP4/12, and Strong Purplish Red, 7.5RP4/11. The inner surface of the inside petal was more brilliant than a color between Moderate Red, 2.5R4/10, and Strong Purplish Red, 10RP4/12. On both the outer and inner surfaces there was a small area at the base between white and Brilliant Yellow Green, 2.5GY9/8.

The general color effect of the newly opened flower is much more brilliant than a color between Strong Red, 5R4/12, and Dark Red, 5R3/7. The bloom after being three days open gives a general color effect which is more brilliant than a color near Moderate Red, 2.5R4/10. The petals drop off cleanly, except for petaloids, and are not particularly affected in this respect by cold, hot, wet or dry weather.

The flower on the bush in the garden often persists for five days or more in the month of August. Cut roses grown outdoors and kept at living-room temperatures will last from three to five days in the month of August.

Reproductive organs

The stamens are average in number, arranged regularly about the pistils, a few being mixed with petaloids.

The filaments are short to medium-length and are generally between Moderate Orange Yellow, 10YR8/10, and Strong Orange, 5YR7/11, in color. Most are with anthers.

The anthers are from small to medium size, and all open approximately at once. The color of the margins is generally between Moderate Orange Yellow, 7.5YR8/8, and Strong Orange, 5YR7/11, sometimes blushed with near Deep Purplish Red, 10RP3/10. Near the point of attachment of the filament the color is generally near Pale Orange Yellow, 7.5YR9/4, sometimes blushed with near Deep Purplish Red, 10RP3/10.

Pollen is moderate, and generally between Moderate Orange Yellow, 7.5YR8/8, and Strong Orange, 5YR7/11, in color.

There are from few to an average number of pistils for miniatures, there being approximately 38 of them.

The styles are uneven, of average length, thin to average caliper, and somewhat loosely bunched. In color, they are off-white near the ovary, becoming a color between Strong Red, 2.5R5/12, and Moderate Red, 2.5R4/10, near the stigma.

The stigma is near Strong Purplish Pink, 7.5RP7/10, in color.

Usually most of the ovaries protrude from the calyx.

Hips are of average length and more or less pear-shaped. At approximately one-third maturity, they are between Strong Yellow Green, 7.5GY7/9, and Strong Yellow Green, 5GY6/8, in color. They are moderately prickly and glandular, with moderately thick, fleshy walls.

Sepals are relatively permanent, moderately short to medium-length, spear-shaped and recurved. Inside, the coloration is between Strong Yellow Green, 5GY7/10, and Moderate Yellow Green, 5GY5/6, lightly overlaid with tomentum. Outside, the coloration is between Strong Yellow Green, 5GY6/8, and Moderate Yellow Green, 5GY5/6.

There are from a few to an average number of seeds, these being small to medium size and from 1 to 6 in number.

THE PLANT

Foliage

The compound leaves usually comprise 3 to 7 leaflets. These are normal to abundant, medium size to large for miniatures, moderately heavy to somewhat leathery, and semi-glossy. The leaflets are ovate in shape, with apex acute, base obtuse, and margin usually doubly serrate.

The mature foliage displays upon its upper surface a coloration which is generally between Moderate Olive Green, 5GY4/3, and Grayish Olive Green, 5GY3/2. The undersurface is near Moderate Yellow Green, 7.5GY5/7, heavily overlaid with a grayish bloom.

The young foliage, on its upper surface, is near Moderate Olive Green, 2.5GY4/3, in color, lightly to moderately overlaid with near Dark Red, 2.5R3/7. The under surface is near Moderate Yellow Green, 5GY5/6, also lightly to moderately overlaid with near Dark Red, 2.5R3/7.

The rachis is average in size, grooved on the upper side, with some stipitate glands on the edges. The under side is sparsely prickly, with stipitate glands.

The stipules are from short to medium-length, medium-width with medium-length points turning out at an angle of usually less than 90°.

The plant displays a more than average resistance to mildew, when compared to other cultivars grown under similar conditions in Southern California.

Growth

The plant is of the dwarf, bushy, upright-spreading habit, much branched. It displays a very vigorous growth. The canes are of medium caliper.

The main stems are generally between Moderate Yellow Green, 7.5GY5/7, and Moderate Olive Green, 7.5GY4/4, in color. They bear several large prickles, which are medium-length to long, almost straight to hooked slightly downward, with medium-length moderately broad bases. There are from several to many small prickles, and both large and small prickles are between Strong Yellowish Brown, 7.5YR5/7, and Moderate Brown, 7.5YR4/5, in color. There are no hairs, but a few stipitate glands.

The branches have a coloration ranging between Strong Yellow Green, 7.5GY7/9, and Moderate Olive Green, 7.5GY4/4. They carry several large prickles, which are medium-length, almost straight to hooked slightly downward, with medium-length moderately broad bases. There are several small prickles, and both large and small prickles are between Dark Orange Yellow, 10YR6/8, and Strong Yellowish Brown, 7.5YR5/7, in color. There are no hairs, but from few to several stipitate glands.

New shoots have a color between Strong Yellow Green, 5GY6/8, and Moderate Yellow Green, 5GY5/6, lightly to moderately overlaid with near Dark Red, 2.5R3/7. There are several large prickles, which are medium-length, almost straight to hooked slightly downward, with medium-length moderately broad bases. There are several small prickles, and both large and small prickles are lighter near their tips, but generally near Moderate Red, 2.5R4/10, in color, although somewhat translucent. There are no hairs, but several stipitate glands.

I claim:

1. A new variety of bush rose of the hybrid miniature moss class, substantially as illustrated and described herein, being particularly characterized by a combination of features including the bearing of many moss-scented stipitate glands on its peduncles, buds, sepals and hips; by the coloration of its flowers, which are of a deep velvety red color, and open relatively slowly with a high pointed center; the petalage of its blooms, which have from about 40 to about 50 petals plus about 7 to 20 petaloids; and the tendency to bloom throughout the growing season.

* * * * *

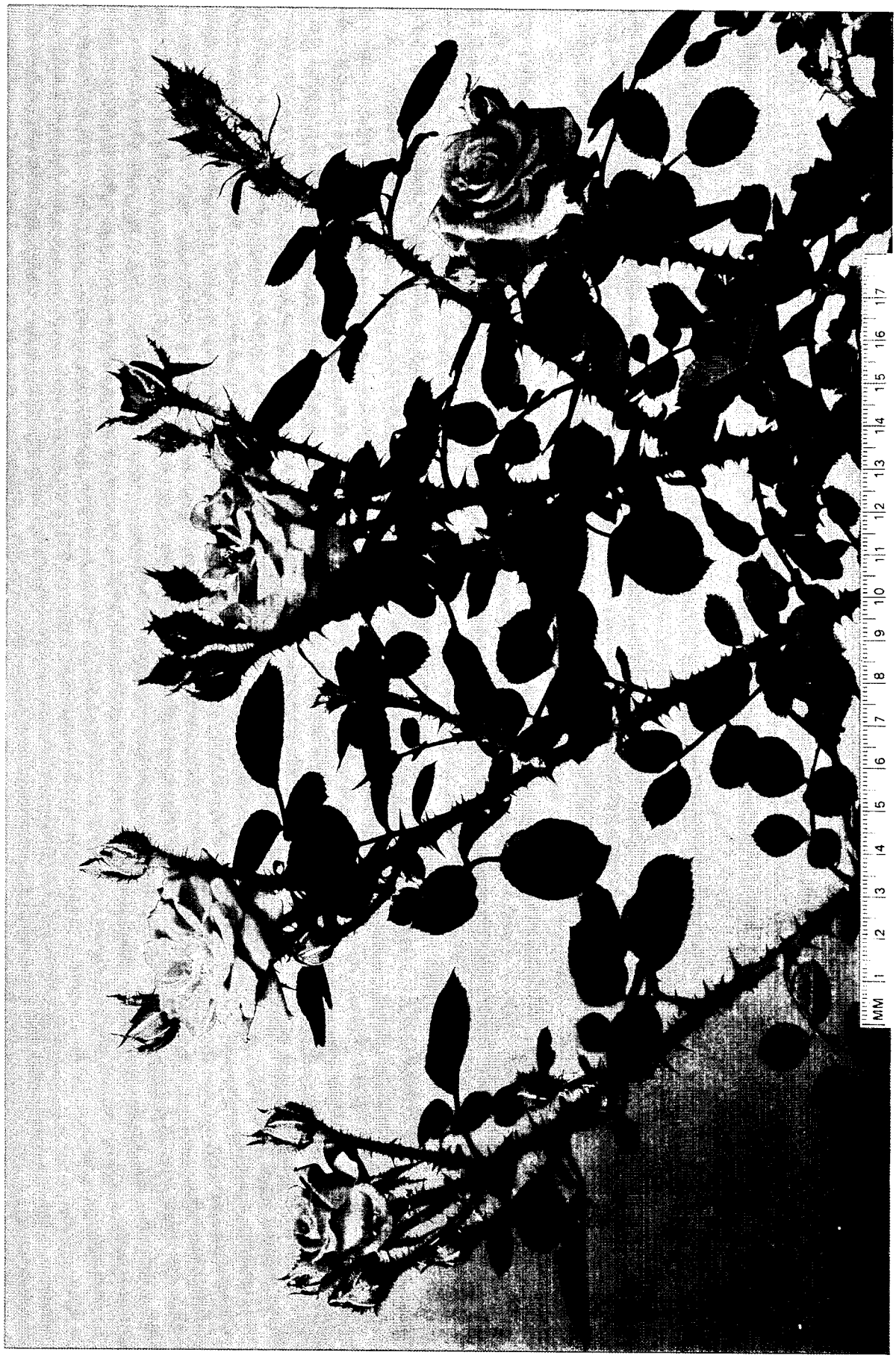
MM
1
2
3
4
5
6
7
8
9
10
11
12
13
14
15
16
17